US010596069B2

(12) United States Patent
Goodman et al.

(10) Patent No.: US 10,596,069 B2
(45) Date of Patent: Mar. 24, 2020

(54) SYRINGES WITH MIXING CHAMBER IN A REMOVABLE CAP

(71) Applicant: Ethicon, Inc., Somerville, NJ (US)

(72) Inventors: John Goodman, Ann Arbor, MI (US); Leo B. Kriksunov, Ithaca, NY (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 184 days.

(21) Appl. No.: 14/978,260

(22) Filed: Dec. 22, 2015

(65) Prior Publication Data

US 2017/0172848 A1 Jun. 22, 2017

(51) Int. Cl.
*A61J 1/20* (2006.01)
*A61M 5/24* (2006.01)
(Continued)

(52) U.S. Cl.
CPC ....... *A61J 1/2096* (2013.01); *A61B 17/00491* (2013.01); *A61M 5/2448* (2013.01); *A61M 5/3145* (2013.01); *B01F 5/0685* (2013.01); *B01F 5/0695* (2013.01); *B01F 13/0023* (2013.01); *B01F 15/0225* (2013.01); *B01F 15/0237* (2013.01); *A61B 2017/00495* (2013.01); *A61M 5/3294* (2013.01); *A61M 2005/3104* (2013.01)

(58) Field of Classification Search
CPC .............. A61M 5/2448; A61M 5/3145; A61M 2005/3104; A61M 5/3294; A61B 17/00491; A61B 2017/00495; B01F 5/0685; B01F 5/0695; B01F 13/0023; B01F 15/0225; B01F 15/0237

USPC .................................................... 141/319, 10
See application file for complete search history.

(56) References Cited

U.S. PATENT DOCUMENTS 1,157,439 A * 10/1915 Starr ................... A61M 5/1408
604/80
2,724,383 A * 11/1955 Lockhart ............... A61J 1/2089
604/204

(Continued)

FOREIGN PATENT DOCUMENTS

EP 1466572 B1 1/2008
EP 2754430 7/2014
(Continued)

OTHER PUBLICATIONS

International Search Report re: PCT/US2016/066846 dated Mar. 27, 2017.
Written Opinion re: PCT/US2016/066846 dated Mar. 27, 2017.

*Primary Examiner* — Timothy L Maust
*Assistant Examiner* — James R Hakomaki
(74) *Attorney, Agent, or Firm* — David R. Crichton; Leo B. Kriksunov

(57) ABSTRACT

The present invention is directed to a multi-compartment medical device for segregated storage and on demand mixing of at least two components and expression of the resulting mixture from the device. The mixing device comprises a syringe having an open end and outlet and containing a first component; and a cap with a fixed outer body and an expandable chamber contained therein, wherein said cap is removably attached to the outlet of the syringe and a cross-section of the cap is larger than a syringe cross-section and the cap is shorter than the syringe.

11 Claims, 18 Drawing Sheets

(51) Int. Cl.
   *A61M 5/31*    (2006.01)
   *B01F 15/02*   (2006.01)
   *B01F 13/00*   (2006.01)
   *B01F 5/06*    (2006.01)
   *A61B 17/00*   (2006.01)
   *A61M 5/32*    (2006.01)

(56) References Cited

U.S. PATENT DOCUMENTS

| | | | |
|---|---|---|---|
| 2,816,690 A * | 12/1957 | Lari | B65D 83/0061 |
| | | | 222/386.5 |
| 3,190,619 A * | 6/1965 | Penney | B01F 15/0225 |
| | | | 366/129 |
| 3,214,067 A * | 10/1965 | Linington | F16N 11/00 |
| | | | 222/341 |
| 3,552,604 A * | 1/1971 | Gordon | B65D 35/02 |
| | | | 222/215 |
| 3,678,931 A * | 7/1972 | Cohen | A61M 5/284 |
| | | | 604/201 |
| 4,172,457 A | 10/1979 | Choksi et al. | |
| 4,863,454 A * | 9/1989 | LaBove | A61J 1/2089 |
| | | | 604/416 |
| 4,991,742 A * | 2/1991 | Chang | A61M 5/148 |
| | | | 222/105 |
| 5,125,415 A * | 6/1992 | Bell | A61M 5/3145 |
| | | | 215/DIG. 3 |
| 5,167,631 A * | 12/1992 | Thompson | A61M 5/152 |
| | | | 222/386.5 |
| 5,346,476 A * | 9/1994 | Elson | A61M 5/148 |
| | | | 604/135 |
| 5,364,369 A * | 11/1994 | Reynolds | A61J 1/2089 |
| | | | 604/187 |
| 5,425,580 A * | 6/1995 | Beller | A61M 31/005 |
| | | | 366/131 |
| 5,566,729 A | 10/1996 | Grabenkort et al. | |
| 5,697,918 A * | 12/1997 | Fischer | A61J 1/2096 |
| | | | 433/90 |
| 5,810,778 A * | 9/1998 | Hjertman | A61M 5/1454 |
| | | | 604/143 |
| 5,876,372 A * | 3/1999 | Grabenkort | A61M 5/31596 |
| | | | 604/89 |
| 5,908,054 A * | 6/1999 | Safabash | A61J 1/2096 |
| | | | 141/100 |
| 6,062,722 A * | 5/2000 | Lake | B01F 5/0615 |
| | | | 366/130 |
| 6,308,747 B1 * | 10/2001 | Farris | A61J 1/067 |
| | | | 141/25 |
| 6,527,738 B1 * | 3/2003 | Jones | A61M 5/1409 |
| | | | 604/84 |
| 6,699,229 B2 | 3/2004 | Zinger et al. | |
| 6,723,131 B2 | 4/2004 | Muschler | |
| 6,811,056 B2 * | 11/2004 | Gabes | B64D 11/04 |
| | | | 222/103 |
| 7,101,354 B2 * | 9/2006 | Thorne, Jr. | A61M 5/31596 |
| | | | 604/191 |
| 7,135,027 B2 | 11/2006 | Delmotte | |
| 7,322,956 B2 | 1/2008 | Fehr et al. | |
| 7,878,704 B2 * | 2/2011 | Bonnard | B01F 5/0685 |
| | | | 366/149 |
| 8,177,740 B1 * | 5/2012 | McGlothlin | A61M 5/152 |
| | | | 604/82 |
| 8,226,627 B2 | 7/2012 | Fowles et al. | |
| 9,550,025 B2 * | 1/2017 | Dunne | A61M 5/2033 |
| 2002/0101785 A1 * | 8/2002 | Edwards | B01F 5/0685 |
| | | | 366/268 |
| 2002/0182718 A1 * | 12/2002 | Malmquist | B01F 11/0082 |
| | | | 435/287.2 |
| 2003/0032935 A1 | 2/2003 | Damiano, Jr. et al. | |
| 2003/0225378 A1 * | 12/2003 | Wilkie | A61B 17/00491 |
| | | | 604/221 |
| 2005/0155901 A1 | 7/2005 | Krueger et al. | |
| 2006/0142701 A1 * | 6/2006 | Thorne, Jr. | A61M 5/31596 |
| | | | 604/218 |
| 2008/0212399 A1 * | 9/2008 | Bonnard | B01F 5/0685 |
| | | | 366/139 |
| 2008/0249498 A1 * | 10/2008 | Fangrow | A61J 1/2096 |
| | | | 604/411 |
| 2008/0264261 A1 * | 10/2008 | Kavazov | A61J 1/2096 |
| | | | 96/193 |
| 2009/0247985 A1 * | 10/2009 | Melsheimer | A61B 17/12022 |
| | | | 604/506 |
| 2010/0246316 A1 * | 9/2010 | Delmotte | A61B 17/00491 |
| | | | 366/133 |
| 2011/0189059 A1 * | 8/2011 | Boehm | A61C 9/0026 |
| | | | 422/225 |
| 2011/0224648 A1 | 9/2011 | Secci | |
| 2013/0345626 A1 * | 12/2013 | Tennican | A61M 5/002 |
| | | | 604/89 |
| 2014/0114276 A1 | 4/2014 | Schweiss et al. | |
| 2014/0135831 A1 | 5/2014 | White et al. | |
| 2014/0144940 A1 | 5/2014 | Delmotte | |
| 2014/0171861 A1 | 6/2014 | Stroumpoulis | |
| 2014/0194887 A1 * | 7/2014 | Shenoy | A61B 17/8811 |
| | | | 606/94 |
| 2015/0190770 A1 * | 7/2015 | Greter | B05C 17/00593 |
| | | | 222/135 |
| 2015/0250463 A1 * | 9/2015 | Jamiolkowski | A61B 17/00491 |
| | | | 604/500 |
| 2015/0290078 A1 | 10/2015 | Li et al. | |
| 2015/0297834 A1 * | 10/2015 | Buder | A61M 5/007 |
| | | | 604/508 |
| 2015/0320641 A1 * | 11/2015 | Fangrow | A61J 1/2089 |
| | | | 137/799 |
| 2015/0320904 A1 * | 11/2015 | Yoo | A61L 26/0052 |
| | | | 606/214 |
| 2016/0114097 A1 * | 4/2016 | Lizari Illarramendi | |
| | | | A61M 5/152 |
| | | | 141/10 |
| 2016/0120527 A1 * | 5/2016 | Larsen | A61L 26/009 |
| | | | 604/518 |
| 2016/0121097 A1 * | 5/2016 | Steele | A61M 39/20 |
| | | | 138/89 |
| 2016/0243317 A1 * | 8/2016 | Asano | A61M 5/36 |
| 2016/0271330 A1 * | 9/2016 | Rhinehart | A61M 5/178 |

FOREIGN PATENT DOCUMENTS

| | | |
|---|---|---|
| JP | 2010172575 A * | 8/2010 |
| WO | WO 2005/123162 | 12/2005 |

* cited by examiner

SYRINGES WITH MIXING CHAMBER IN A REMOVABLE CAP

FIELD OF THE INVENTION

The present invention relates to multi-compartment medical devices for segregated storage and on demand mixing of at least two components and for expressing the resulting mixture from the device for use in treating a patient. The invention further relates to methods of segregated storage and on demand mixing of at least two components and for expressing the resulting mixture from the device. The invention further relates to devices for and methods of reconstituting lyophilized materials.

BACKGROUND OF THE INVENTION

Currently there are a number of biomedical applications where there is a need to rapidly and thoroughly mix two or more components in the operating room substantially immediately prior to administration to the patient. The mixing of components can typically involve extraction of one component in fluid form from a vial or other container and transfer of such component into a separate container which holds another component. In particular instances, only a portion of the contents of a vial or container is to be utilized for preparing a mixture prior to administering. Accordingly, the extraction and transfer can involve precise measuring of one or more components to be mixed.

A variety of problems can occur when utilizing conventional methodology and devices for mixing and/or administering biomedical agents to an individual. For example, where multiple components are to be mixed, extraction and transfer of one component and introduction of such component into another component can potentially expose one or both of the components to a non-sterile or contaminated environment leading to contamination of the resulting mixture. Additionally, incomplete extraction or improper measurement of one or more components can result in preparation and/or administration of an improper dosage. In particular instances, once biomedical agents are mixed the mixture must again be extracted from a vial or container into a syringe prior to administering to an individual. Such additional transfer can lead to additional opportunities for contamination, incomplete extraction of contents and/or inaccurate measuring of a component or the resulting biomedical agent.

In practice, there is limited availability of sterile environments for maintaining sterility during transfer and/or mixing of components, or preparation and transfer of biomedical agents. Additional errors can result from use of the wrong diluent to reconstitute the medication. Finally, preparation of biomedical agents utilizing multiple components can be tedious and time consuming due to factors such as the need to access individually packaged items such as separate vials and/or transfer devices, or to measure one or more components to be combined to form the biomedical agent. The multiple packaging and storage containers such as separate vials and/or transfer devices increase the cost of care and also create an additional waste stream which has to be dealt with in accordance with regulations governing the disposal of biomedical waste. There is a need in a simplified system for segregated storage and rapid and thorough mixing of two or more components in the operating room substantially immediately prior to administration to the patient, which can also reduce the risk of contamination during preparation.

Preparation of injectable drugs or hemostatic agents often requires a thorough mixing of two or more components which are stored in separate compartments. Use of multiple vials and syringes is expensive and wasteful, complicates the preparation, increases the probability of error, and requires proper disposal of used containers. For example, in preparation of a hemostatic paste based on biopolymer, such as gelatin, in mixture with thrombin, the surgeon often performs the mixing by using two interconnected connected syringes and moving the paste back and forth to mix gelatin with saline solution containing thrombin. One syringe is then discarded.

In preparation of reconstituted solution of a protein, such as reconstituted thrombin or fibrinogen from lyophilized thrombin or fibrinogen, the dry lyophilized powders need to be thoroughly mixed when reconstituted with water or saline.

In some commercially available hemostatic kits, reconstitution of lyophilized thrombin is performed in a vial into which water is injected from a syringe. After swirling the mixture, the solution is aspirated back into syringe. The reconstitution of the thrombin can be slow because there is no forced mixing in the vial. Then the solution is expressed into a sterile cup and the syringe and the vial are discarded. The solution is then aspirated by another syringe and can be connected via a luer to the syringe containing the gelatin matrix. The contents are then mixed by moving between syringes back and forth, after which one syringe is discarded and the ready mixture is expressed from the last syringe. The process of using and discarding a vial, a cup, and two syringes to prepare one syringe with the hemostatic paste in multiple sequential steps requires time and high attentiveness of the healthcare professional.

There are a number of known multi-chamber, single barrel as well as multi-barrel syringes which attempt to accomplish the segregated storage of two components and subsequent mixing and expression of the resulting mixture from the syringe.

A number of references disclose two syringes which are interconnected and used for mixing components by moving from the mix from one syringe to another.

None of the references provide, in a single syringe, for the capability of vigorous back and forth mixing between the compartments and thus for rapid effective reconstitution and/or mixing of separately stored components. The known systems utilizing valves are complex and can plug up with the mixing materials, or can leak during storage. Only uni-directional movement of the plunger (i.e. forward) is possible, resulting in insufficiently efficient mixing of the components.

U.S. Published Patent Application 2014/0114276 RECONSTITUTION AND APPLICATOR SYSTEM FOR WOUND SEALANT PRODUCT discloses a system for mixing or reconstituting agents including engageable syringe barrels, one of which having a male engagement region and the other a female engagement region. Each of the male and female engagement regions is provided with a screen. The screens are closely spaced from one another when the first and second syringe barrels are engaged with one another. The screens can take the form of a mesh, a plurality of protuberances, or cantilevered wedges having tapering thicknesses. It further discloses a method for reconstituting a powdered agent comprising: providing a first syringe barrel including a main chamber defined by a cylindrical barrel wall, an open proximal end, and a male engagement region at a distal end, the male engagement region including a screen; providing a second syringe barrel including a main chamber defined by a cylindrical barrel wall, an open proximal end, and a female engagement region at a distal end, the female engagement region including a screen; depositing the powdered agent into the main chamber of one of the first syringe barrel or the second syringe barrel; inserting a plunger in the open proximal end of the first syringe barrel; inserting a plunger in the open proximal end of the second syringe barrel; drawing a diluent into the main chamber of one of the first syringe barrel or the second syringe barrel; engaging the male engagement region of the first syringe barrel with the female engagement region of the second syringe barrel; and tilting the engaged first and second syringe barrels back and forth.

U.S. Pat. No. 5,566,729 entitled Drug reconstitution and administration system, discloses a drug reconstitution and administration system that includes a container for a concentrated drug or other medicament, a syringe assembly which can be pre-filled with a liquid diluent, and a mixing adapter assembly which facilitates mixing of the medicament with the liquid diluent.

U.S. Patent publication No. 2003/0032935 entitled Packages facilitating convenient mixing and delivery of liquids, discloses embolic devices and methods for mixing and delivering embolic material in a sterile environment that facilitate delivery of the embolic material directly into a patient thereby preventing the embolic material from becoming contaminated. Such devices include a sealable container couplable to a syringe, a dissolvable caplet or gel-cap including a solid or liquid embolic material, a sealed vial with a breakable neck containing an embolic material, and a flexible container including internal compartments separated by breakable membranes.

European Patent Publication EP1466572B1 entitled Device for packaging, mixing and applying bone cement discloses a device for packaging, mixing and applying bone cement obtainable from at least one first component and one second component, comprising: a first container, in which the first component is packaged hermetically and which is provided with an opening that is associated with first temporary closure means; a second substantially cylindrical container, which is provided with an outlet that is associated with second temporary closure means; and piston means, which are inserted so that they can slide hermetically within the second container and can be actuated from outside with a rectilinear motion; the second component is packaged between the outlet and the piston means; the opening and the outlet are temporarily mutually associable, and the piston means are suitable to push the second component from the second container to the first container for mixing with the first component and to aspirate the cement thus formed from the first container into the second container.

U.S. Pat. No. 6,723,131 entitled Composite bone marrow graft material with method and kit discloses a kit containing sterilized implements useful in preparing enriched composite bone marrow graft material, kit having two loading syringes attached to a matrix column.

U.S. Patent Publication No. 2011/0224648 entitled Syringe Filter Cap and Method of Using the Same for Administration of Medication Dosage discloses a syringe and filter cap that ease the administration of medication to patients. The cap fits securely over the syringe nozzle and has at least one orifice. The orifice is configured to retain medication particles within the syringe, while allowing liquid to be drawn into the syringe through the cap.

U.S. Pat. No. 8,226,627 entitled Reconstitution assembly, locking device and method for a diluent container, discloses a reconstitution assembly that includes: a flexible bag containing a diluent; a drug vial containing a drug; a reconstitution device further comprising: a first sleeve connected to the first container; a second sleeve connected to the second container, the second sleeve being associated with the first sleeve and movable axially with respect thereto from an inactivated position to an activated position; a piercing member positioned in the sleeves, the piercing member providing a fluid pathway between the bag and vial when the sleeves are in the activated position.

U.S. Pat. No. 6,699,229 entitled Fluid transfer device, discloses a fluid transfer and mixing device for use in the aseptic intermixing of a powder component with a fluid component. The device is of a simple, compact construction that includes a first adapter that can be easily connected to a container containing the powder component and a second adapter that can be removably interconnected with the first adapter and can also be readily connected to a container containing a fluid such as a diluent so as to permit aseptic intermixing of the diluent with the powder. In use a conventional needleless syringe can be easily connected to the first adapter so that the mixture of the powder and diluent can be aseptically aspirated from the first container for subsequent delivery to the patient.

U.S. Patent Publication No. 2005/0155901 entitled surgical cement preparation system, discloses a surgical cement preparation system designed for the rapid, clean, safe, accurate and thorough handling and combining of cement ingredients, particularly useful in the preparation of surgical cements such as polymethylmethacrylate to ensure their thorough mixture and presentation in advance of the cured or hardened state. It provides a surgical cement preparation system for combining a liquid ingredient together with at least one solid powder ingredient comprising a needle and syringe assembly and a mixing vial structured to optimize their relative functions and cooperatively interact with other components.

U.S. Patent Publication No. 2014/0135831 entitled BIO-ADHESIVE MIXING AND PREPARATION SYSTEMS AND METHODS USING TWO SYRINGES, discloses a bioadhesive mixing assembly that includes first and second syringes and an adapter. The first syringe includes first and second chambers holding a first sealant component and an activator, respectively. The second syringe includes third and fourth chambers holding a second sealant component and one of an activator or a third sealant component, respectively. The adapter is mounted to the first syringe and includes first and second channels in flow communication with the first and second chambers, a first seal member providing sealed access to the first and second channels, first and second needles connected in flow communication with the third and fourth chambers, and a second seal member enclosing the first and second needles. Connecting the adapter to the second syringe punctures the first and second seal members with the first and second syringes to create flow communication between the first and third chambers and the second and fourth chambers.

U.S. Pat. No. 7,135,027 titled Devices and methods for mixing and extruding medically useful compositions discloses devices and methods for mixing and extruding compositions which are medically and non-medically useful. The devices are particularly useful for mixing substances which are relatively inert when alone but become reactive when mixed. A common feature of all of the devices is that they allow the user to mix and ultimately extrude a composition from a single device which includes a single container or multiple interconnected containers.

U.S. Pat. No. 7,322,956 titled System and method for mixing at least four components, discloses a system for mixing four components including a first syringe arrangement and a second syringe arrangement each with two chambers for holding components. Each of the two respective chambers of the syringe arrangements are connected in a uniquely defined fashion due to specific means for connecting the syringe arrangements. A component held by one chamber is mixed with a component of the corresponding other chamber by transfer into the other chamber. After mixing and disconnecting the second syringe arrangement from the first syringe arrangement, the two component mixtures in the chambers of the first syringe arrangement are further mixed and discharged by means of a mixing device which is to be connected to the first syringe arrangement. The connecting means allows connecting of the mixing device to the first syringe arrangement only after removal of the second syringe arrangement and a portion of the connecting means.

None of the references provide, for the capability of vigorous back and forth mixing between the compartments and thus for rapid effective reconstitution and mixing of separately stored components. The known systems utilizing valves are complex and can plug up with the mixing materials, or can leak during storage. Only unidirectional movement of the plunger (i.e. forward) is possible, resulting in insufficiently efficient mixing of the components. It would be desirable to develop alternative multi-compartment medical devices for segregated storage and on demand mixing of at least two components and for expressing the resulting mixture from the device for use in treating a patient.

SUMMARY OF THE INVENTION

Briefly, the present invention in one aspect relates to a mixing device comprising: a syringe having an open end and outlet and containing a first component; and a cap with a fixed outer body and an expandable chamber contained therein, wherein said cap is removably attached to the outlet of the syringe and a cross-section of the cap is larger than a syringe cross-section and the cap is shorter than the syringe.

In another aspect, the present invention relates to a method of making and delivering a mixture, comprising: attaching a cap having a fixed outer body and an expandable chamber therein containing a second component to a syringe containing a first component; the cap having larger cross-section than the cross-section of the syringe and the cap being shorter than the syringe; the expandable chamber can expand within the cap to accommodate all of the first and second components; expressing the first component from the syringe into the expandable chamber; retrieving the first component and the second component from the expandable chamber back into the syringe; optionally repeating steps (b) and (c) several times until the first component and the second component are thoroughly mixed; retrieving the first component and the second component from the expandable chamber back into the syringe; detaching the cap from the syringe leaving substantially all of the first component and the second component in the syringe; and expressing the mixed first component and the second component from the syringe onto a target.

DETAILED DESCRIPTION OF THE INVENTION

According to one aspect of the present invention, there is provided a mixing device useful for mixing two or more separately stored components immediately before application to tissue or wound. The mixing device comprises a syringe filled with the first component which is a fluid, suspension, or a paste, and one or more removable caps affixed to the syringe. The removable cap has within it an expandable chamber. The chamber has a moveable piston or an elastic collapsible bag or bladder to accept material from the syringe. The cross-section or the diameter (for round cross-sections) of the chamber is larger than that of the syringe which allows the cap to be substantially shorter than the length of the syringe body. The cross-sections of the chamber or the cap can be round, elliptical, rectangular polygonal, or any other suitable cross-section.

The chamber can contain at least a second component intended for mixing with the first component. The chamber can contain an optional porous mixing or absorbing section. The optional porous section can contain an optional additional releasable component that is released upon contact with the liquid or semi-liquid first component.

Examples of components include one or more of gelatin; saline; thrombin; fibrinogen; oxidized regenerated cellulose powder or any medically useful substance for mixing. In one aspect, first component is gelatin and second component is saline. In one aspect, at least one component is a clotting factor, such as thrombin. In one aspect at least one component is cross-linkable material, such as fibrinogen.

The second component is contained within the expandable chamber in the cap. The optional third component and/or fourth component are contained within the luer connector and/or within the optional porous section and/or within the second cap.

Figure 1A:
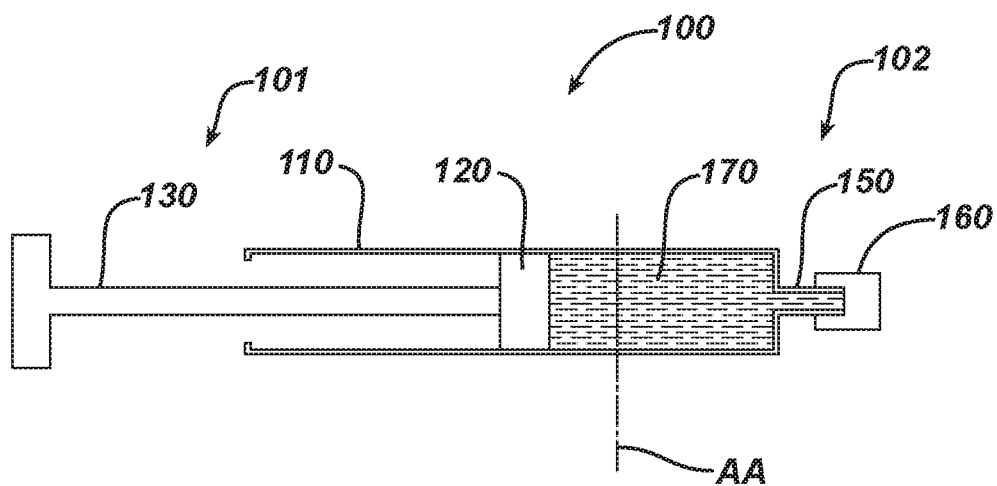
FIGS. 1a and 1b, respectively, show a syringe and an embodiment of mixing cap of the present invention.

Referring to FIG. 1A, a syringe 100 has a hollow syringe body 110, a syringe plunger 120 disposed within syringe body 110 and slidably movable inside syringe body 110 when actuated by an elongated syringe handle 130 attached to syringe plunger 120, syringe handle 130 extending from syringe body 110 at a syringe proximal end 101. Syringe body 110 is terminated at a syringe distal end 102 with a syringe nozzle 150 capped by a syringe stopper 160. Syringe 100 is at least partially filled with a first component 170.

Figure 1B:
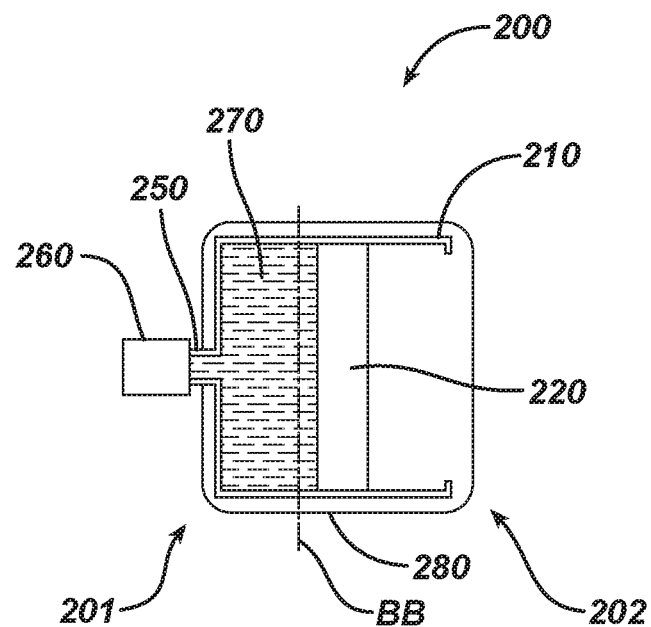

Referring to FIG. 1B, a cap 200 is configured to be attached onto and detached from syringe nozzle 150. In one aspect, cap 200 comprises a hollow cap body 210, a cap piston 220 disposed within cap body 210 and slidably movable inside cap body 210 from a proximal end 201 to a distal end 202. Cap body 210 with cap piston 220 is enclosed in an optional cap housing 280 which encapsulates cap body 210. At proximal end 201 of cap housing 280 there is a cap nozzle 250 capped by a cap stopper 260.

Cap body 210 is at least partially filled with a second component 270 with the second component being held within cap body 210 in the area between cap nozzle 250 and cap piston 220 which forms an expandable chamber.

First and second components 170 and 270 can be liquid, semi-liquid (paste), or solid, with at least one of components being either liquid or semi-liquid.

Figure 1C:
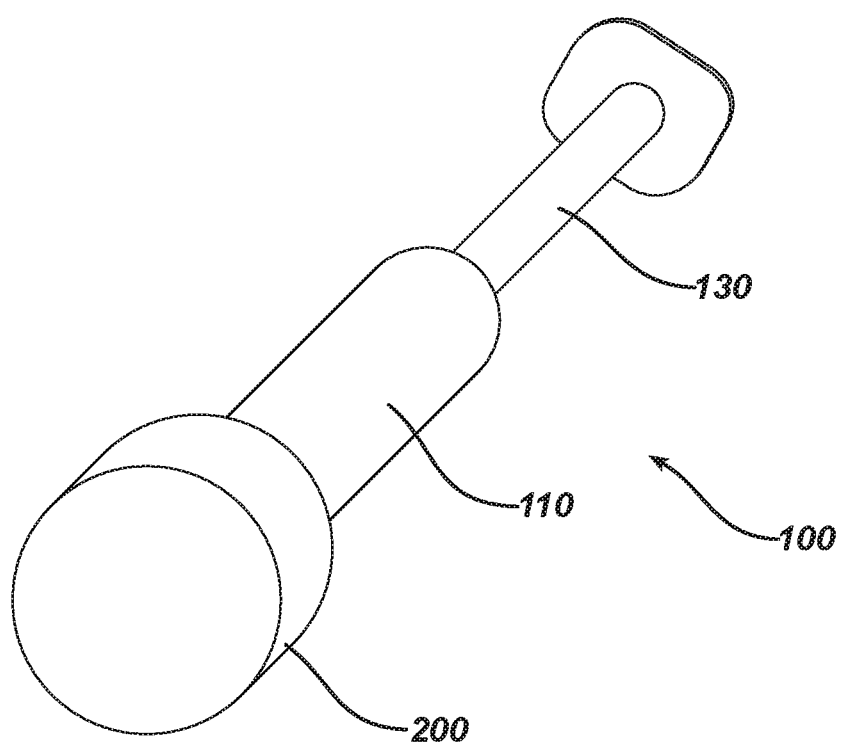
FIG. 1c shows a schematic perspective view of syringe connected to mixing cap of the present invention.
Figure 2:
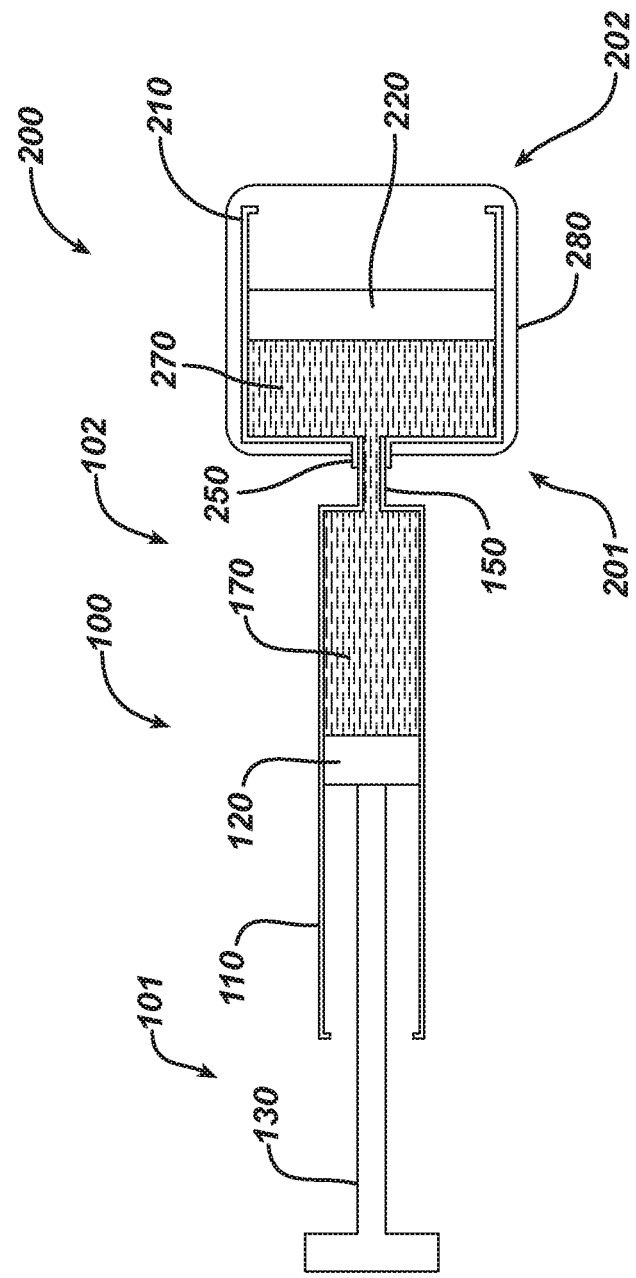
FIG. 2 shows syringe connected to mixing cap of the present invention.

Referring to FIGS. 1c and 2, syringe 100 is shown connected to cap 200 with cap nozzle 250 engaged with syringe nozzle 150 by any known interconnection mechanism, such as by snap-on joint or by a threaded screw-on joint, or similar. The connection of syringe 100 to cap 200 is performed after removal of syringe stopper 160 and cap stopper 260. Connecting of syringe 100 to cap 200 enables mixing of first and second components 170 and 270 by moving syringe plunger 120 using syringe handle 130 back and forth between syringe proximal end 101 and syringe distal end 102. Moving syringe plunger 120 towards syringe distal end 102 is displacing first component 170 to cap body 210 mixing first component 170 with second component 270, with cap piston 220 moving towards cap distal end 202.

Figure 3:
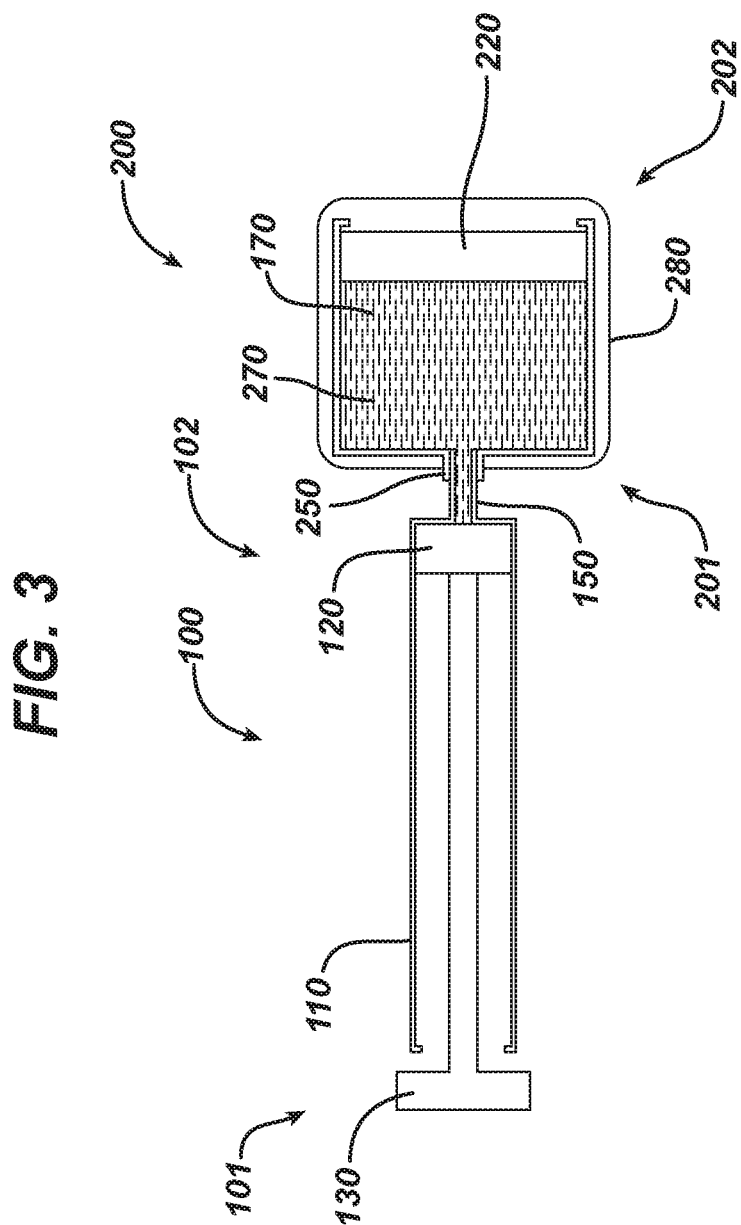
FIG. 3 shows syringe connected to mixing cap of the present invention in operation.

Referring to FIG. 3, in operation, syringe plunger 120 is moved using syringe handle 130 towards syringe distal end 102 displacing all first component 170 to cap body 210, mixing first component 170 with second component 270. Cap piston 220 is shown being moved towards cap distal end 202, with cap body 210 accommodating combined volumes of first component 170 and second component 270.

Figure 4:
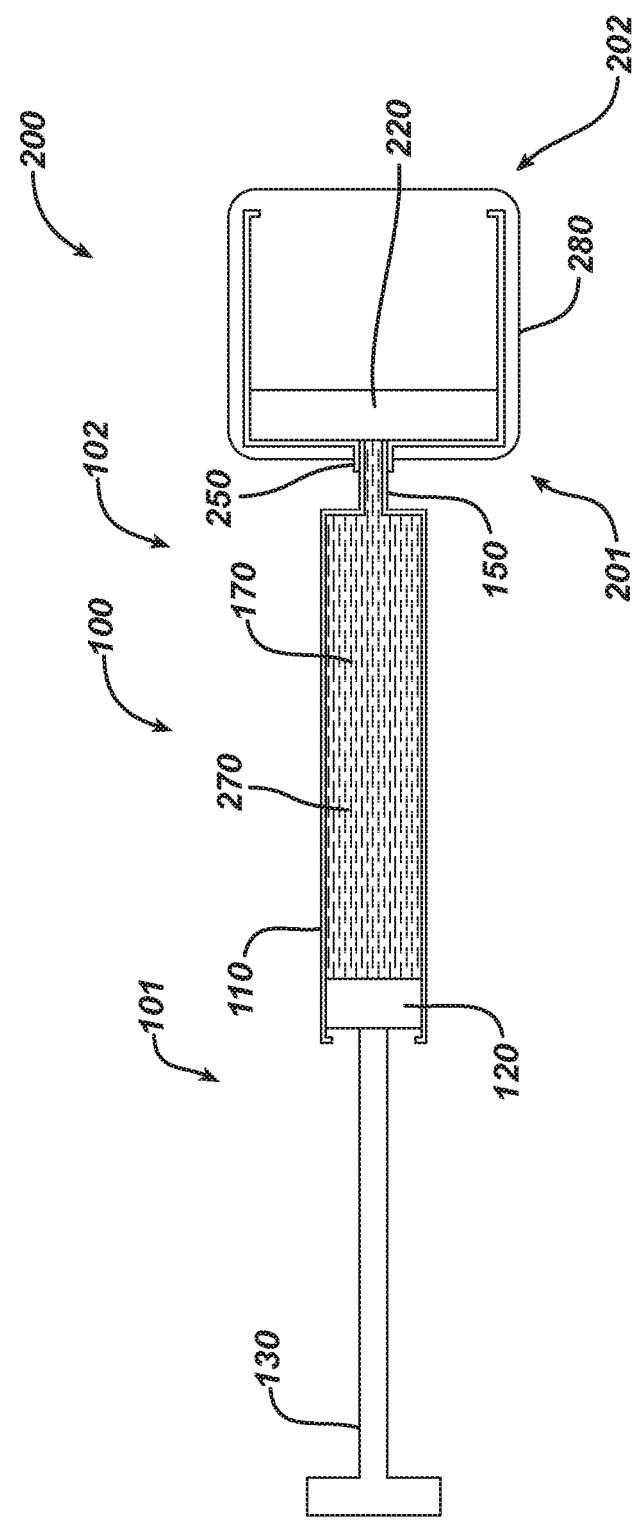
FIG. 4 shows syringe connected to mixing cap of the present invention in operation.

Referring to FIG. 4, in continued operation, syringe plunger 120 is moved using syringe handle 130 towards syringe proximal end 101 pulling all first component 170 and second component 270 from cap body 210 into syringe body 110. As first component 170 and second component 270 transfer from cap 200 to syringe 100 through syringe nozzle 150 and cap nozzle 250 first component 170 and second component 270 continue to intermix.

In continued operation, syringe plunger 120 is again moved towards syringe distal end 102 displacing all first component 170 and second component 270 to cap body 210, resulting in position depicted earlier in FIG. 3. As first component 170 and second component 270 transfer from syringe 100 to cap 200 through syringe nozzle 150 and cap nozzle 250 first component 170 and second component 270 continue to intermix.

In operation, the steps described above are repeated several times, such as 1, 2, 3, 4, 5, 6, 7, 8, 9, 10 or more times, moving syringe plunger 120 back and forth between syringe distal end 102 and syringe proximal end 101 and thus moving first component 170 and second component 270 from syringe body 110 to cap body 210 and back, whereby first component 170 thoroughly mixes with second component 270.

After moving syringe plunger 120 back and forth between syringe distal end 102 and syringe proximal end 101 and thus moving mixture of first component 170 and second component 270 from syringe body 110 to cap body 210 and back several times, first component 170 is thoroughly mixed with second component 270. Syringe plunger 120 is then pulled towards syringe proximal end 101 thus transferring all or substantially all mixed first component 170 and second component 270 into syringe 100 as illustrated in FIG. 4. Cap 200 is then disconnected from syringe 100. Syringe 100, now containing substantially all mixture of first component 170 and second component 270 is then directed towards tissue or wound and is used to express mixed first component 170 and second component 270 onto tissue or wound, either directly through syringe nozzle 150 or through an appropriate attachment nozzle or cannula or drip tip or spray tip.

Cap body 210 is configured to be able to accommodate all volume of first component 170 and second component 270 combined. Syringe body 110 is configured to be able to accommodate all volume of first component 170 and second component 270 combined.

Cap body 210 has cross-section substantially larger than cross-section of syringe body 110. Cross-section of syringe body 110 is defined as area formed by plane AA shown in FIG. 1A by a dashed line, with plane AA dissecting syringe body 110 perpendicularly to direction of movement of syringe plunger 120. Cross-section of cap body 210 is defined as area formed by plane BB shown in FIG. 1B by a dashed line, with plane BB dissecting cap body 210 perpendicularly to direction of movement of cap piston 220.

In case of round cross-sections, cap body 210 has diameter substantially larger than the diameter of syringe body 110. Preferably, cap body 210 cross-section or diameter is at least 1.5 times larger relative to the cross-section or diameter of syringe body 110, such as 2 times larger, 2.5 times larger, 3 times larger, 4 times larger, 5 times larger, or similar. Cap body 210 length from proximal end 201 to distal end 202 is substantially shorter than syringe body 110 length from proximal end 101 to distal end 102.

In one aspect, cap body 210 inside diameter or inside cross-section is 2 times larger relative to the inside diameter or inside cross-section of syringe body 110. The displacement of syringe plunger 120 within syringe body 110 of 10 cm results in displacement of cap piston 220 of about 2.5 cm. Cap housing 280 length from cap proximal end 201 to cap distal end 202 is configured to accommodate displacement of cap piston 220 of about 2.5 cm, with cap housing 280 length being in one aspect in the range from 2.7 cm to 3.5 cm, such as 3 cm.

In one aspect, cap body 210 inside diameter or inside cross-section is 3 times larger relative to the inside diameter or inside cross-section of syringe body 110. The displacement of syringe plunger 120 within syringe body 110 of 9 cm results in displacement of cap piston 220 of 1 cm. Cap housing 280 length from cap proximal end 201 to cap distal end 202 is configured to accommodate displacement of cap piston 220 of about 1 cm, with cap housing 280 length being in one aspect in the range 1.2 cm to 2 cm, such as 1.5 cm.

In one aspect, cap housing 280 is opaque.

Figure 5:
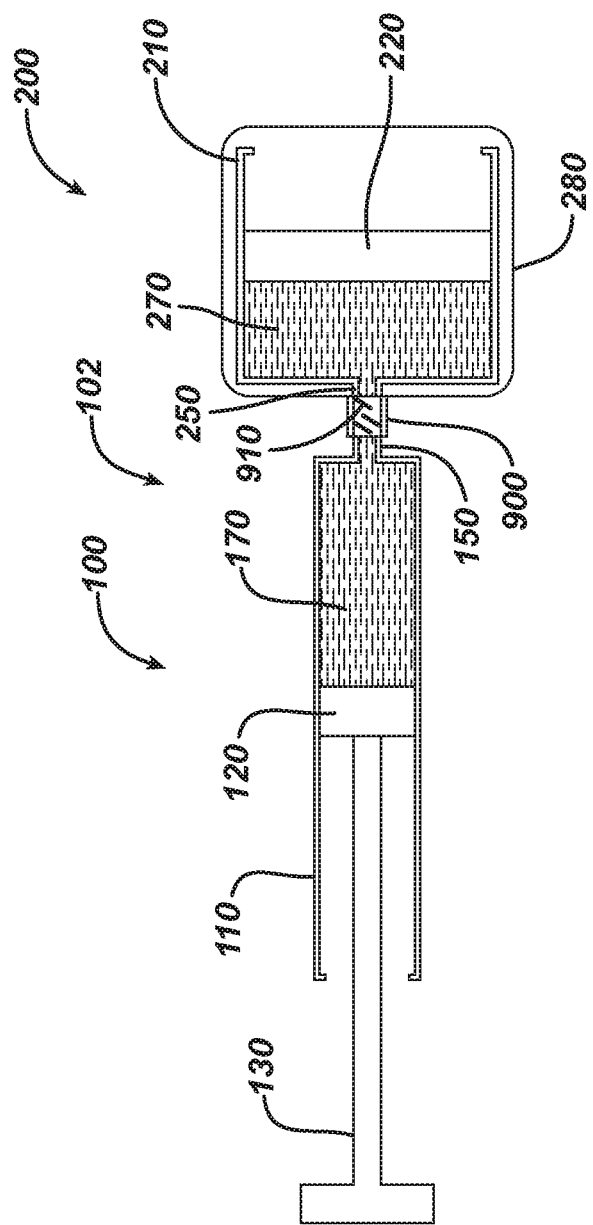
FIG. 5 shows syringe connected to mixing cap of the present invention via connector luer.

Referring to FIG. 5, in one aspect, there is provided an optional luer connector 900 configured for interconnecting cap nozzle 250 to syringe nozzle 150. In one aspect, there are provided optional static mixing elements or baffles or porous plug or filter within one or more of cap nozzle 250; syringe nozzle 150, and/or luer 900. In one aspect, there are static mixing elements or baffles 910 installed within luer 900 as shown in FIG. 5, creating a tortuous path resulting in more turbulence and/or turns in the flow of mixed first component 170 and second component 270, thus facilitating further intermixing. In other aspects, optional static mixing elements or baffles are installed within cap nozzle 250 or syringe nozzle 150 (optional mixing elements or baffles not shown installed within cap nozzle 250 or syringe nozzle 150).

Figure 6:
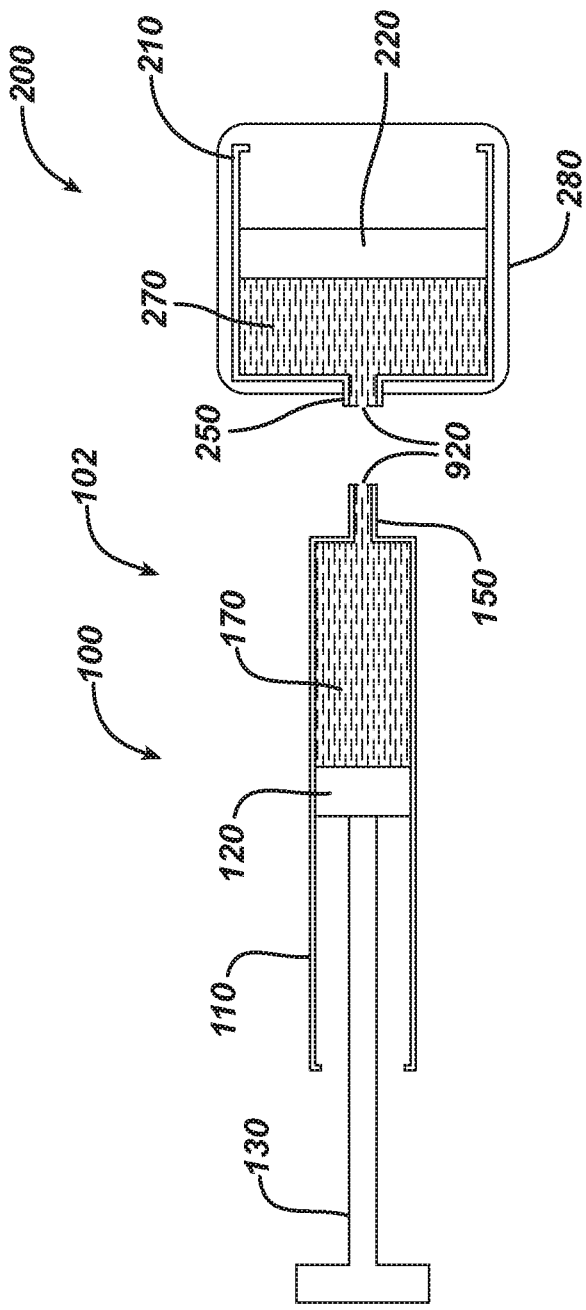
FIG. 6 shows embodiments of syringe and mixing cap of the present invention.

In one aspect, there are provided optional flow restricting valves at cap nozzle 250 and/or syringe nozzle 150, preventing inadvertent loss of first component 170 or second component 270 or their mixture when syringe 100 is disconnected from cap 200. Referring to FIG. 6, optional flow restricting valves 920 comprise membranes with at least one slit or fine aperture installed at the exits of cap nozzle 250 and/or syringe nozzle 150. Optional flow restricting valves 920 enable fluids to move into and from syringe 100 and cap 200 under pressure or vacuum generated by moving plunger 120, but prevent drips of fluids to exit syringe 100 and cap 200 when no pressure or vacuum is applied. In one aspect, cap nozzle 250 and/or syringe nozzle 150 are optionally covered by optional foil seals or flip lids (not shown) to allow for storage and easy opening or foil breakage upon connecting or upon expression.

In one aspect, cap housing 280 is sealed so that as cap piston 220 moves towards cap distal end 202, cap housing 280 is pressurized and resistance to movement of cap piston 220 towards cap distal end 202 increases. Once exerting pressure on syringe handle 130 towards syringe distal end 102 stopped or syringe handle 130 is being moved towards syringe proximal end 101, pressure within cap housing 280 pushes cap piston 220 towards cap proximal end 201 helping moving mixture of components 170 and 270 from cap 200 to syringe 100.

Figure 7A:
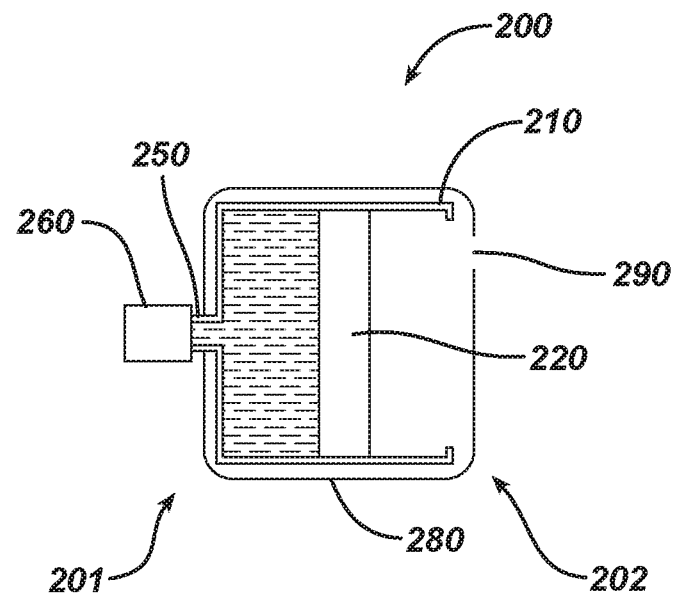
FIGS. 7a and 7b show embodiments of mixing cap of the present invention.

In another aspect, as shown in FIG. 7A, an optional pressure relief aperture 290 is provided in cap housing 280, preventing pressure or vacuum build-up within cap housing 280.

Figure 7B:
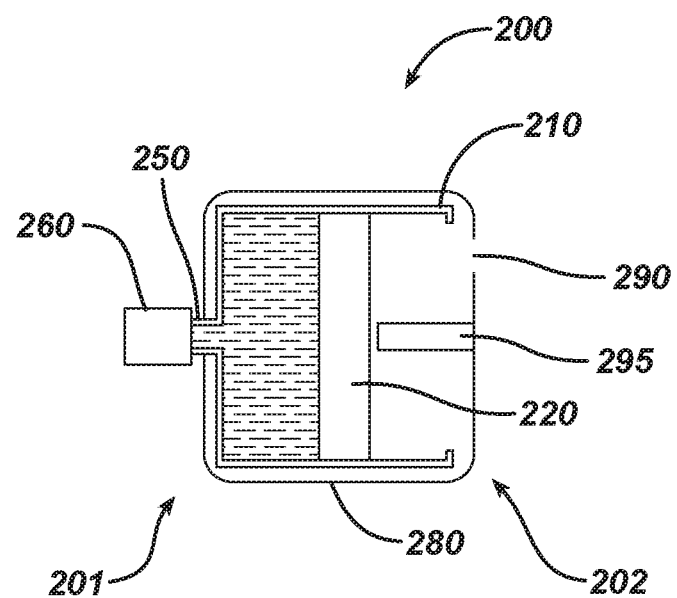

In yet another aspect, as shown in FIG. 7B, there is provided an optional spring 295 positioned in cap housing 280 so as to exert pressure on cap piston 220, with no pressure or fully relaxed spring in the initial or storage position of cap piston 220. As cap piston 220 moves towards cap distal end 202 spring 295 compresses and resistance to movement of cap piston 220 towards cap distal end 202 increases. Once exerting pressure on syringe handle 130 towards syringe distal end 102 stopped or syringe handle 130 is being moved towards syringe proximal end 101, spring 295 pushes cap piston 220 towards cap proximal end 201 helping moving mixture of components 170 and 270 from cap 200 to syringe 100. Pressure relief aperture 290 can be employed (as shown in FIG. 7B) or not employed (not shown in FIG. 7B) when spring 295 is utilized. In some embodiments spring 295 is pre-loaded, i.e. it exerts pressure on cap piston 220, with spring 295 somewhat compressed even in the initial or storage position of cap piston 220.

Optional spring 295 or pressure build up inside cap housing 280 in the absence of optional pressure relief aperture 290 creates a pressure on cap piston 220 pushing cap piston 220 towards cap proximal end 201. This helps return movement of the piston and prevents gas bubbles forming in the fluid due to vacuum formation.

Figure 8:
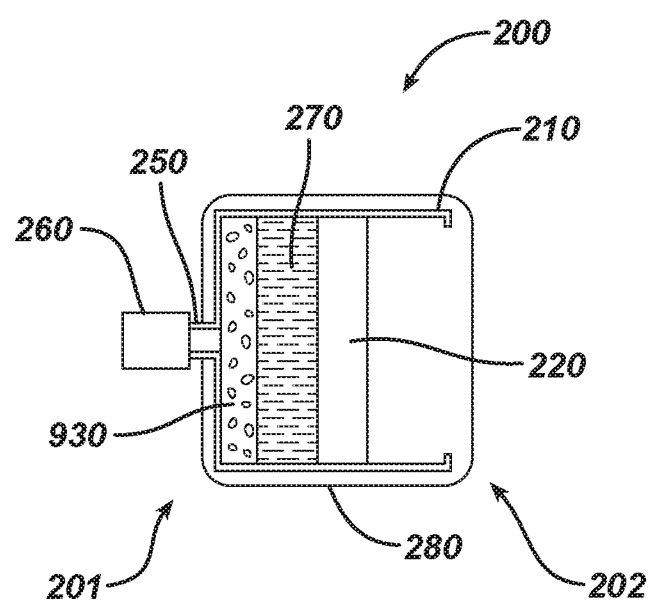
FIG. 8 shows an embodiment of mixing cap of the present invention.
Figure 9:
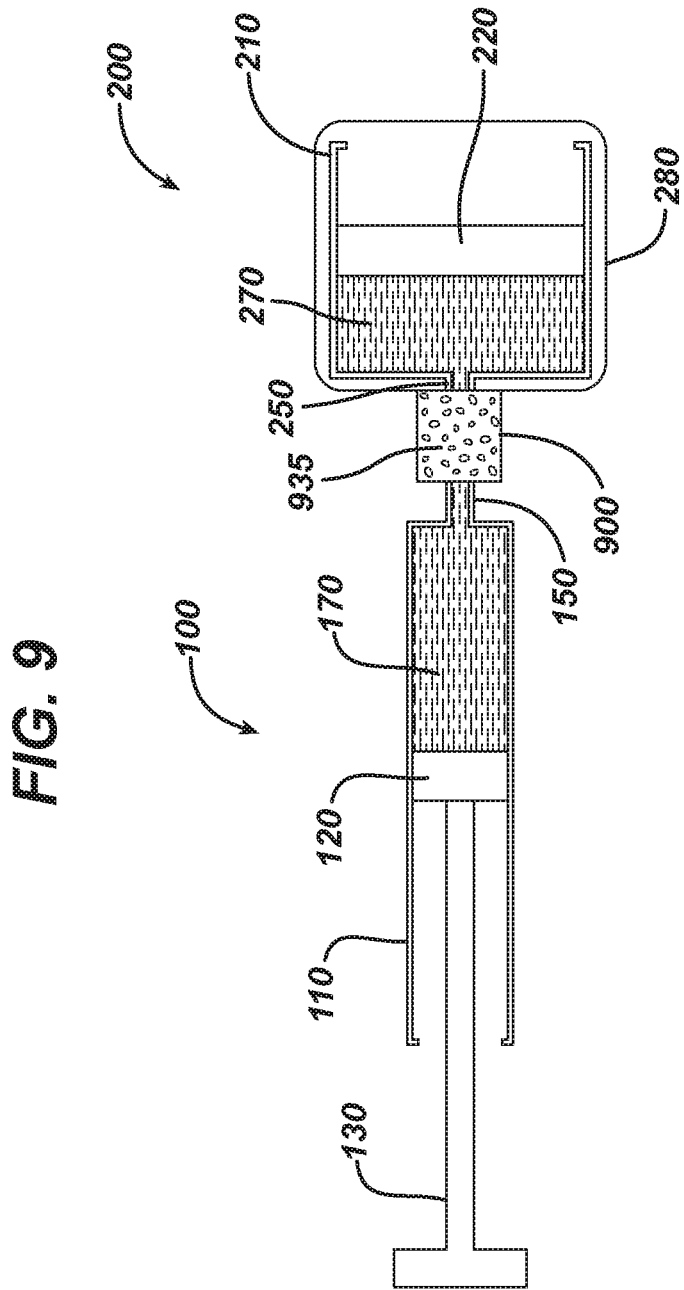
FIG. 9 shows syringe connected to mixing cap of the present invention via connector luer.

In one aspect, there is an optional porous absorption or desorption section within the cap 200 or within the luer connector 900. Referring to FIG. 8, cap porous section 930 is positioned inside cap body 210 at cap proximal end 201. Referring to FIG. 9, a luer porous section 935 is inside luer 900. Porous section, such as luer porous section 935 or cap porous section 930 is configured to absorb or remove from first component 170 stabilizing or clotting preventing factors. Luer porous section 935 or cap porous section 930 alternatively is configured to release clotting factors into first component 170.

Figure 10:
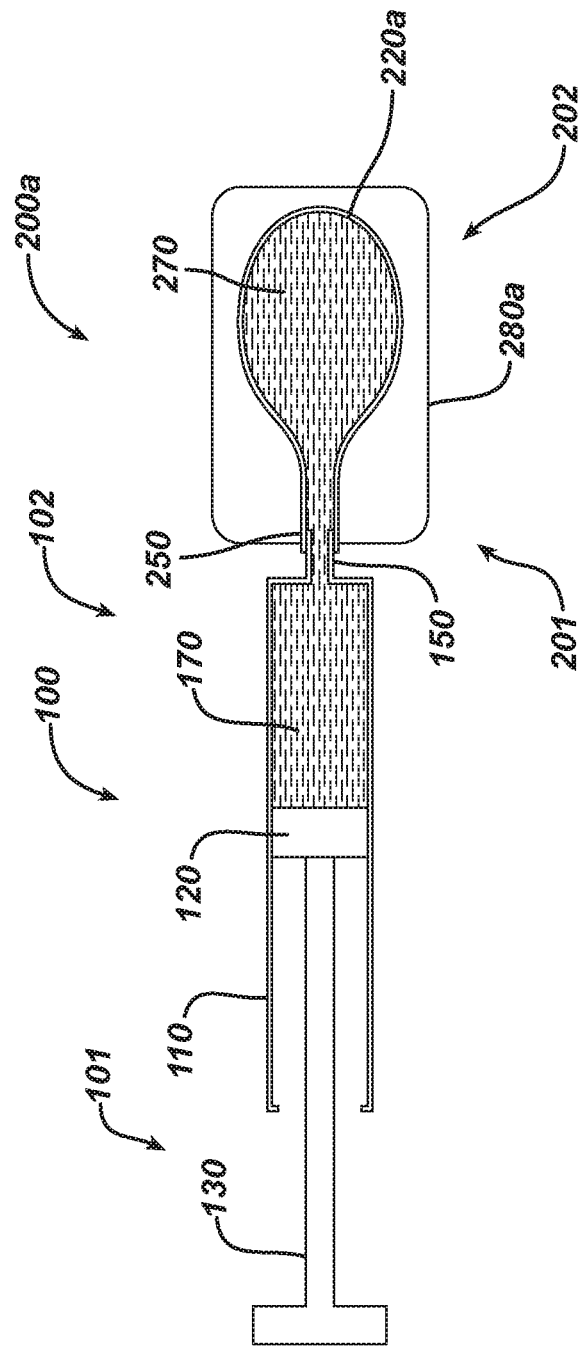
FIG. 10 shows syringe connected to an embodiment of mixing cap of the present invention.
Figure 11:
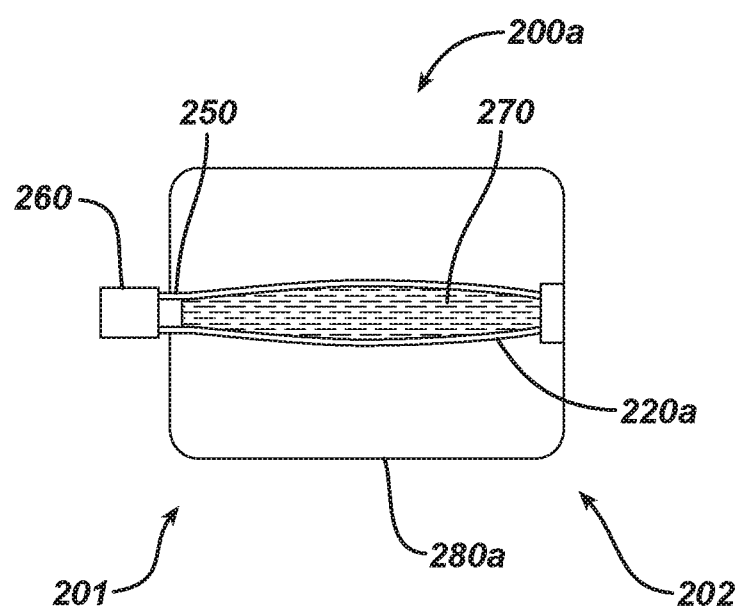
FIG. 11 shows an embodiment of mixing cap of the present invention.

Referring to FIGS. 10 and 11, cap 200a with elastic expandable chamber is configured to be attached onto and detached from syringe nozzle 150. In one aspect, cap 200a comprises an elastic and expandable bladder 220a disposed within and enclosed in cap housing 280a. At proximal end 201 of cap housing 280a there is a cap nozzle 250. Bladder 220a is at least partially filled with a second component 270 with bladder 220a forming an expandable chamber.

In FIG. 10, syringe 100 is shown connected to cap 200a with cap nozzle 250 engaged with syringe nozzle 150 by any known interconnection mechanism, such as by snap-on joint or by a threaded screw-on joint, or similar. Connecting of syringe 100 to cap 200a enables mixing of first and second components 170 and 270 by moving syringe plunger 120 using syringe handle 130 back and forth between syringe proximal end 101 and syringe distal end 102. Moving syringe plunger 120 towards syringe distal end 102 is displacing first component 170 to expandable bladder 220a mixing first component 170 with second component 270. FIG. 10 shows bladder 220a at least partially expanded accepting at least a portion of first component 170.

Figure 12:
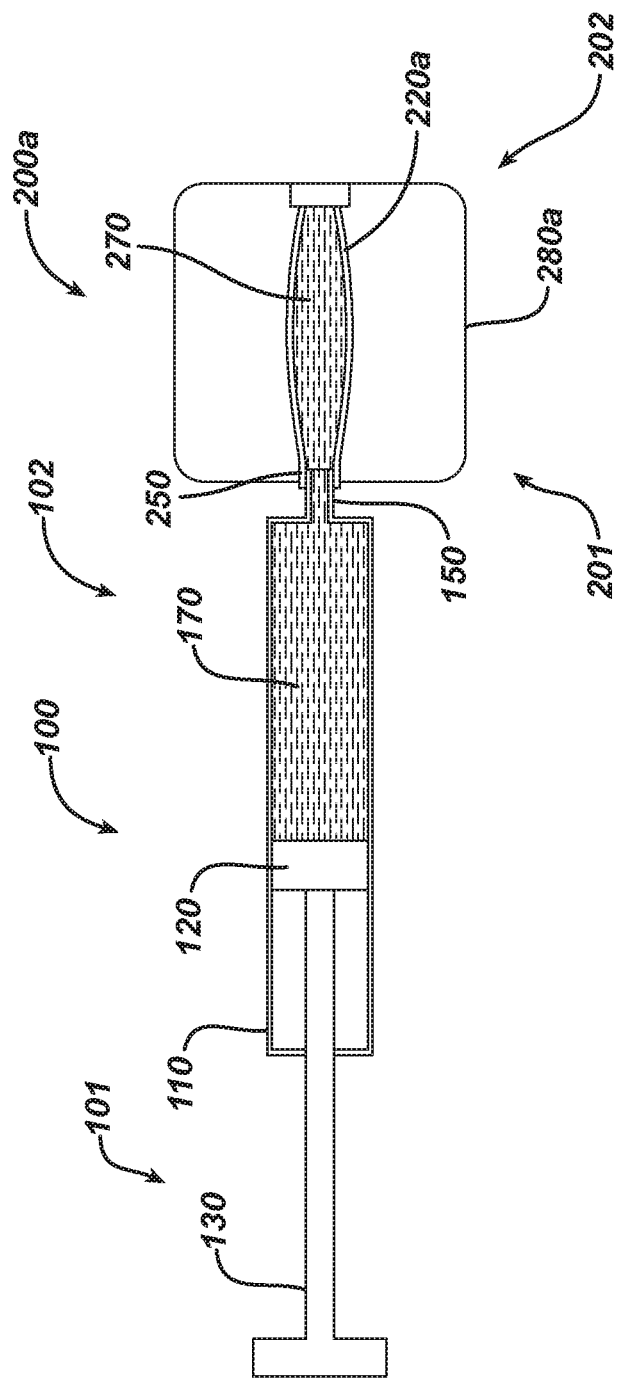
FIG. 12 shows syringe connected to mixing cap of the present invention.

Referring further to FIG. 11, at proximal end 201 of cap housing 200a there is a cap nozzle 250 capped by a cap stopper 260 when cap 200a is in storage. Bladder 220a is shown in an unexpanded state and contains second component 270. Referring to FIG. 12, in operation, after removing cap stopper 260, cap is connected to syringe nozzle 150, with bladder 220a in unexpanded state. Syringe plunger 120 is then moved using syringe handle 130 towards syringe distal end 102 displacing first component 170 to bladder 220a, mixing first component 170 with second component 270 inside expanding bladder 220a which is accommodating combined volumes of first component 170 and second component 270, as shown in FIG. 13.

Figure 14:
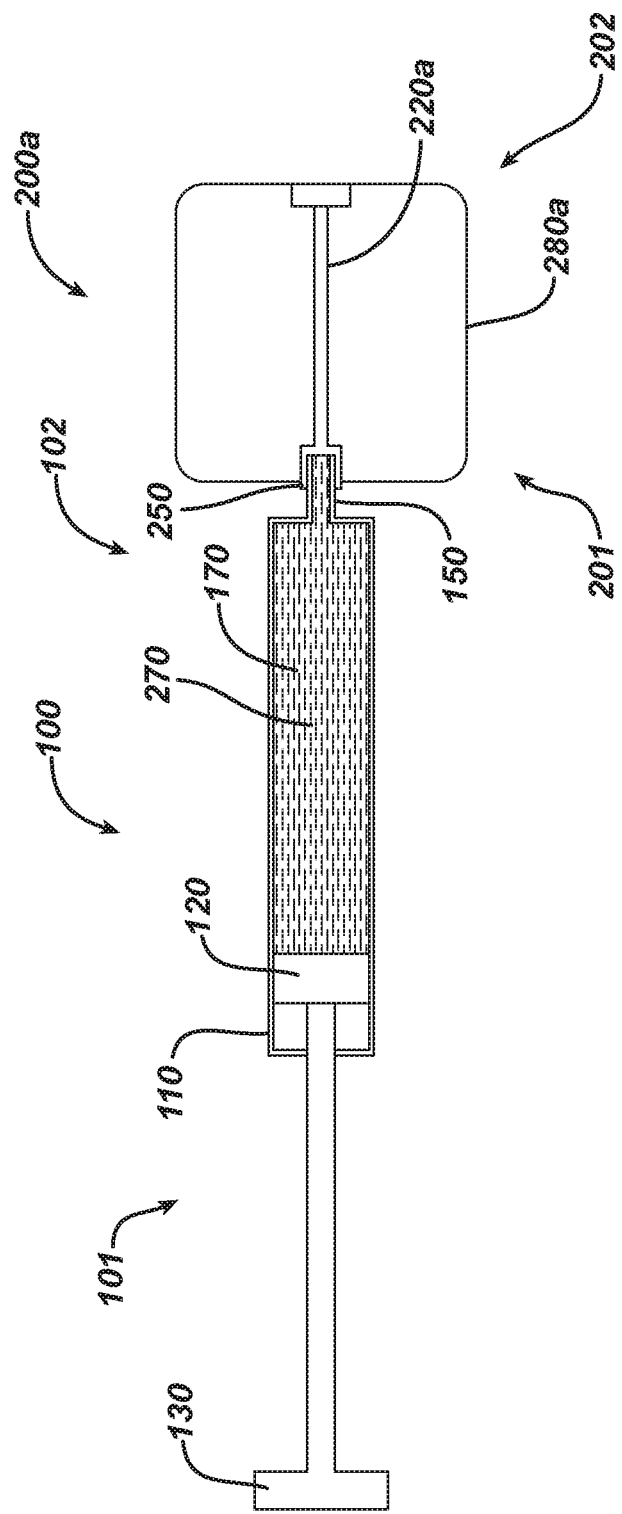
FIG. 14 shows syringe connected to mixing cap of the present invention in operation.

Referring to FIG. 14, in continued operation, syringe plunger 120 is moved using syringe handle 130 towards syringe proximal end 101 pulling all first component 170 and second component 270 from cap 200a into syringe body 110 and fully or at least partially collapsing bladder 220a. The expandable chamber comprising an elastic collapsible bladder that is self-collapsible. As first component 170 and second component 270 transfer from cap 200a to syringe 100 through syringe nozzle 150 and cap nozzle 250 first component 170 and second component 270 continue to intermix.

Figure 13:
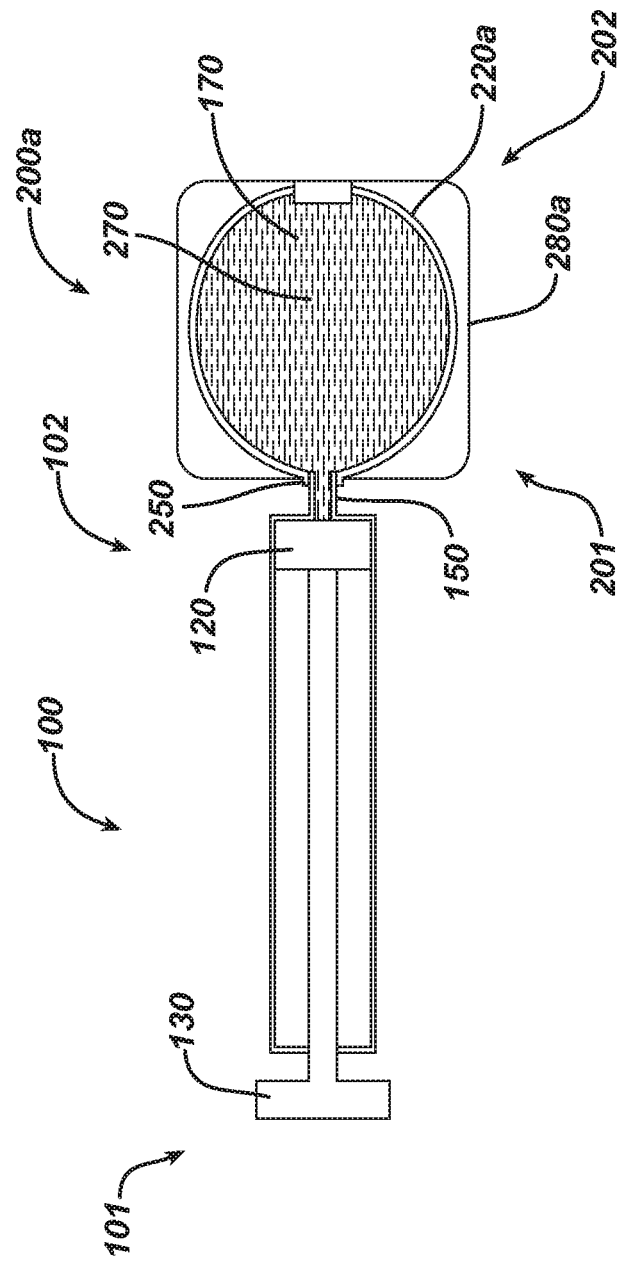
FIG. 13 shows syringe connected to mixing cap of the present invention in operation.

In continued operation, syringe plunger 120 is again moved towards syringe distal end 102 displacing all first component 170 and second component 270 to cap 200a as shown in FIG. 13. As first component 170 and second component 270 transfer from syringe 100 to cap 200a through syringe nozzle 150 and cap nozzle 250 first component 170 and second component 270 continue to intermix.

In further operation, the steps described above are repeated several times, such as 1, 2, 3, 4, 5, 6, 7, 8, 9, 10 or more times, moving syringe plunger 120 back and forth between syringe distal end 102 and syringe proximal end 101 and thus moving first component 170 and second component 270 from syringe body 110 to cap 200a and back, whereby first component 170 thoroughly mixes with second component 270.

After moving syringe plunger 120 back and forth between syringe distal end 102 and syringe proximal end 101 and thus moving mixture of first component 170 and second component 270 from syringe body 110 to cap body 210 and back a number of times appropriate for full intermixing of components, first component 170 is thoroughly mixed with second component 270. Syringe plunger 120 is then pulled towards syringe proximal end 101 thus transferring all or substantially all mixed first component 170 and second component 270 into syringe 100 as illustrated in FIG. 14. Cap 200a is then disconnected from syringe 100. Syringe 100, now containing substantially all first component 170 and second component 270 is then directed towards tissue or wound and is used to express mixed first component 170 and second component 270 onto tissue or wound, either directly through syringe nozzle 150 or through an appropriate attachment nozzle or cannula or drip tip or spray tip.

Bladder 220a is configured to be able to accommodate all volume of first component 170 and second component 270 combined. Syringe body 110 is configured to be able to accommodate all volume of first component 170 and second component 270 combined. Cap 200a has a cross-section substantially larger than the cross-section of syringe body 110. In case of round cross-sections, cap 200a has diameter substantially larger than the diameter of syringe body 110. Cap 200a is substantially shorter than syringe body 110.

Similarly to the embodiments shown above, in some aspects, there is an optional porous absorption or desorption section within the cap 200a or within the luer connector 900 (not shown). Cap porous section can be positioned inside cap 200a at cap proximal end 201. Porous section, such as luer porous section or cap 200a porous section, is configured to absorb or remove from first component 170 stabilizing or clotting preventing factors. Luer porous section or cap 200a porous section alternatively is configured to release clotting factors into first component 170.

Figure 15:
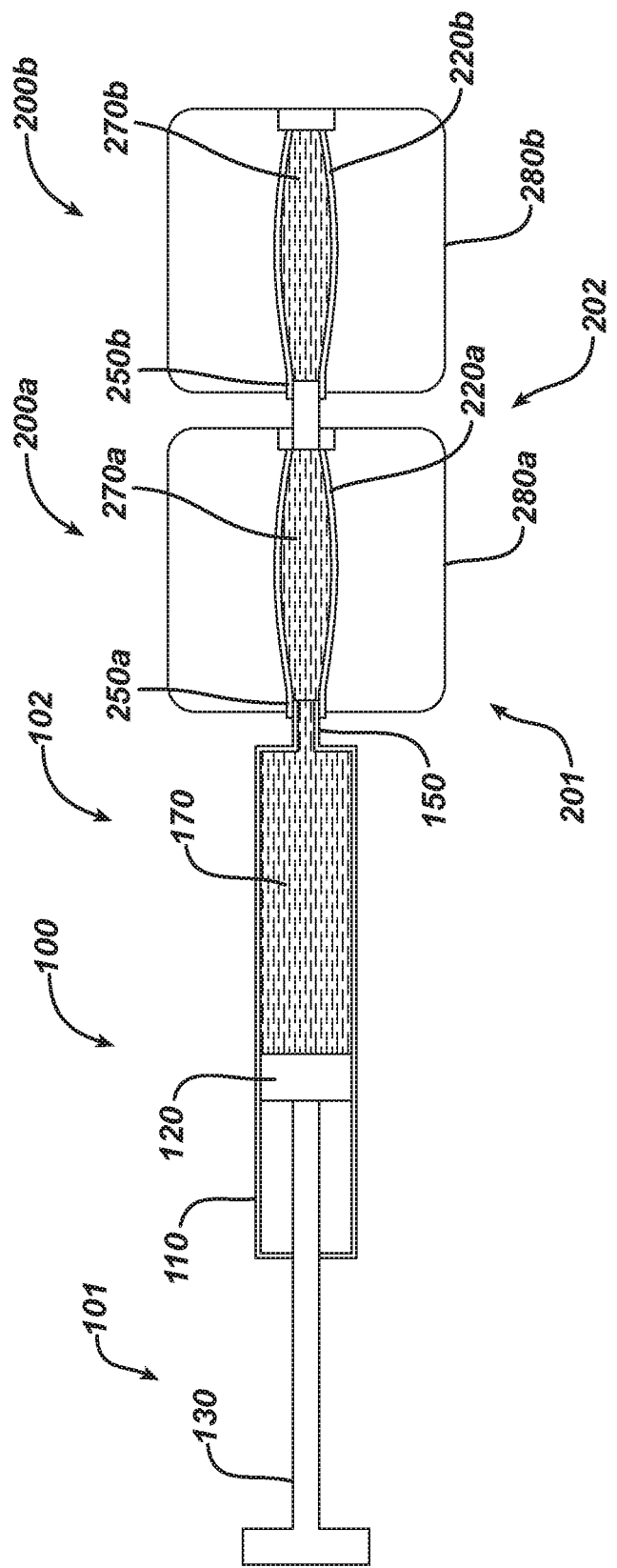
FIG. 15 shows syringe connected to two mixing caps of the present invention in series.

In some aspects of the present invention, there are two or more caps attached to syringe 100, each cap containing a different component 270a, 270b to be mixed with first component 170. Referring to FIG. 15, first cap 200a is shown attached to nozzle 150, while second cap 200b is shown attached to rear port 250b positioned at first cap 200a distal end 202, with both first cap 200a and second cap 200b having expandable bladders 220a and 220b. In this aspect of the present invention, first cap 200a has cap nozzle 250a at proximal end 201 and rear port 250b at distal end 202. Second cap 200b has only cap nozzle 250b.

Figure 16:
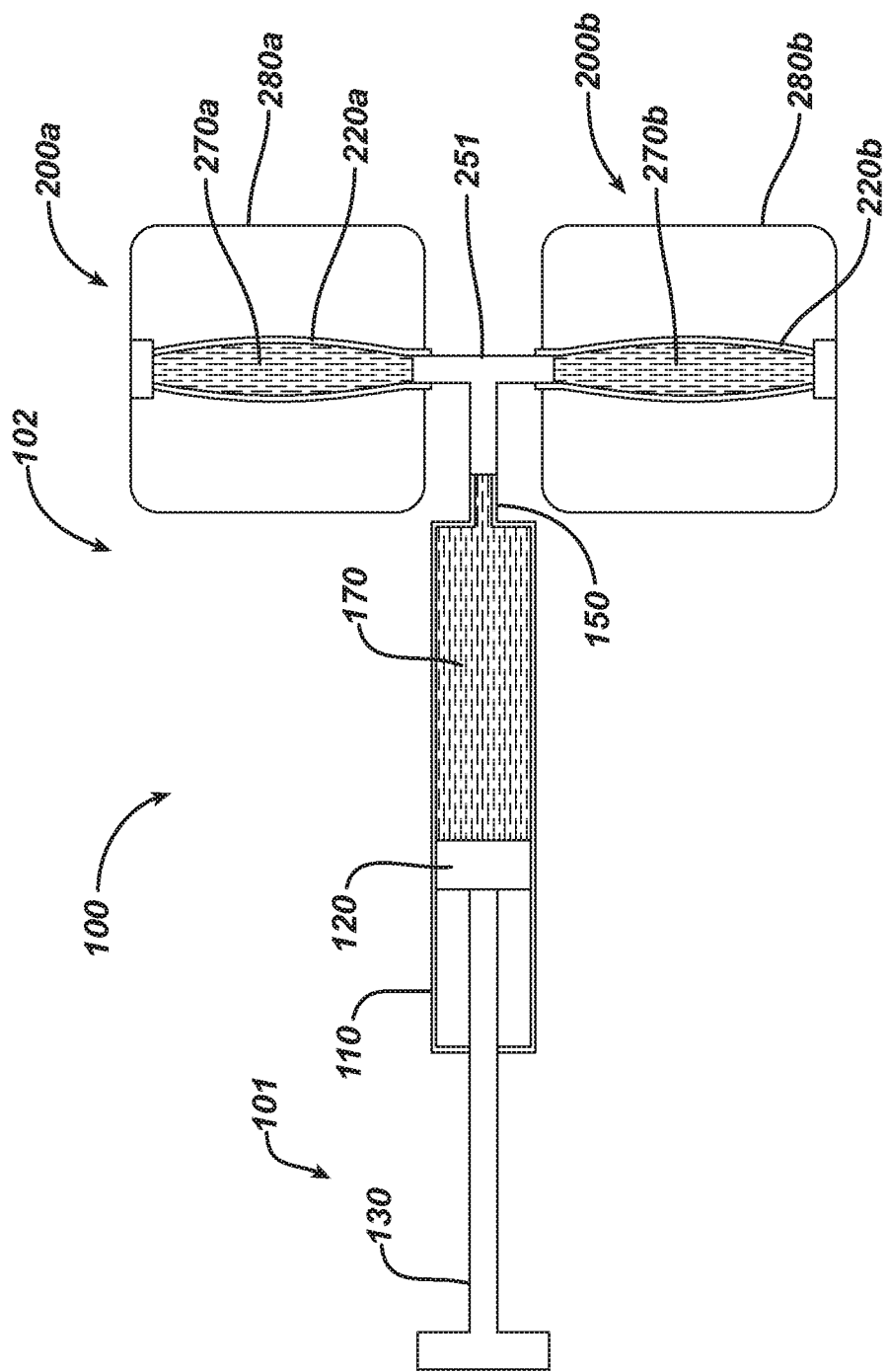
FIG. 16 shows syringe connected to two mixing caps of the present invention in parallel.

In other aspects of the present invention, as shown in FIG. 16, two or more caps are attached to syringe 100 via any multi-port connector or manifold, such as shown "T" shaped connector 251, each cap containing a different component 270a, 270b to be mixed with first component 170. First cap 200a is shown attached to nozzle 150, while second cap 200b is shown attached to rear port 250b positioned at first cap 200a distal end 202.

In operation of embodiments shown in FIGS. 15 and 16, syringe plunger 120 is moved towards syringe distal end 102 and back displacing first component 170 into bladders 220a and 220b and then withdrawing first component 170, second component 270a, and third component 270b back into syringe 100. As first component 170, second component 270a, and third component 270b transfer from syringe 100 to caps 200a and 200b and back through syringe nozzle 150 all components continue to intermix.

After moving syringe plunger 120 back and forth between syringe distal end 102 and syringe proximal end 101 and thus moving mixture of first component 170 and components 270a and 270b from syringe body 110 to caps 200a and 200b a number of times appropriate for full intermixing of components, syringe plunger 120 is then pulled towards syringe proximal end 101 thus transferring all or substantially all mixed components 170, 270a, 270b into syringe 100. Caps 200a, 200b are then disconnected from syringe 100, and T shaped connector 251 of the embodiment shown in FIG. 16 also disconnected from syringe 100. Syringe 100, now containing substantially all mixed components 170, 270a, and 270b is then directed towards tissue or wound and is used to express mixed components onto tissue or wound, either directly through syringe nozzle 150 or through an appropriate attachment nozzle or cannula or drip tip or spray tip.

Figure 17:
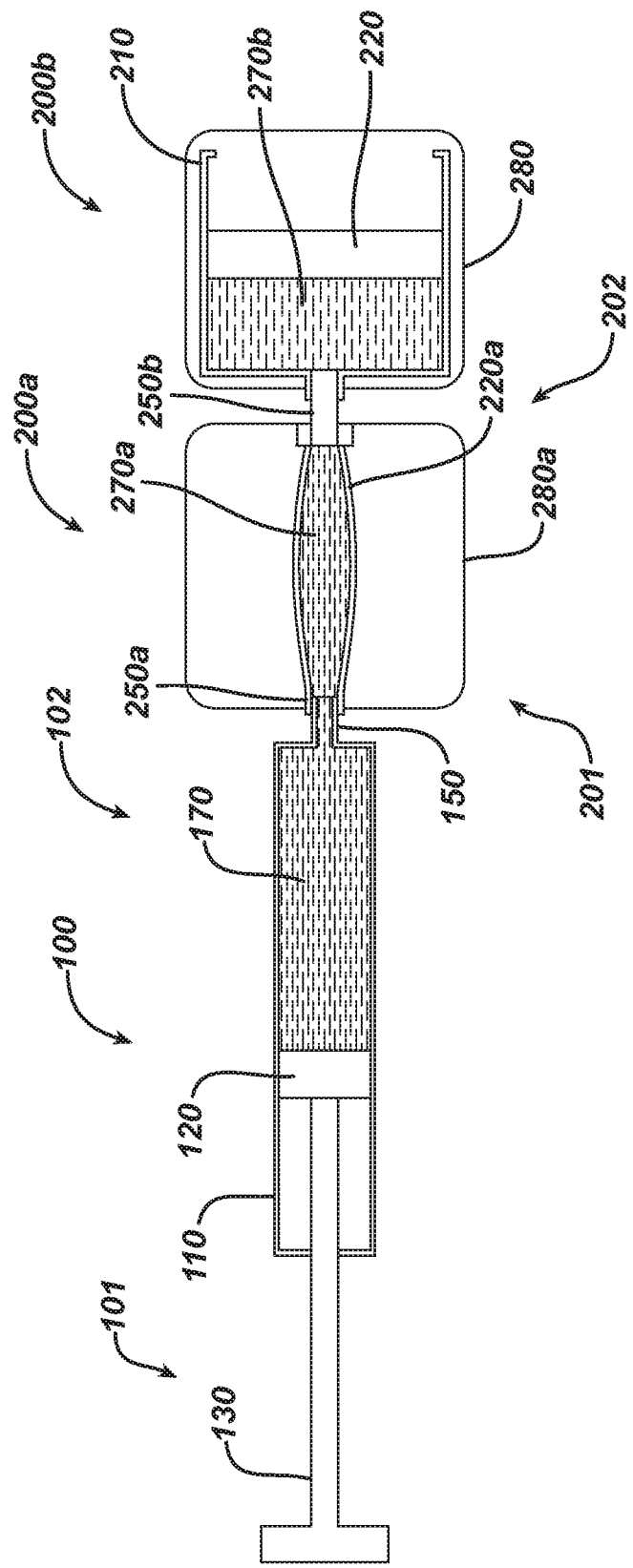
FIG. 17 shows syringe connected to two mixing caps of the present invention in series.

In an alternative aspect of the present invention, there are two or more caps attached to syringe 100, each cap containing a different component 270a, 270b to be mixed with first component 170, with first cap 200a having bladder 220a and second cap 200c having cap piston 220. In one embodiment (not shown), both caps 200a and 200c are connectable to nozzle 150 via a manifold, similarly to the arrangements shown in FIG. 16. In another embodiment, similar to the embodiment of FIG. 15 and shown in FIG. 17, first cap 200a with bladder 220a is attached to nozzle 150, while second cap 200c with cap piston 220 is shown attached to rear port 250b positioned at first cap 200a distal end 202. In this aspect of the present invention, first cap 200a has cap nozzle 250a at proximal end 201 and rear port 250b at distal end 202.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A mixing device comprising:
a syringe having an open end and outlet and containing a first component which is a fluid; and
a cap with a fixed outer body and an expandable chamber contained therein that contains a second component which is a fluid, a powder, or a paste,
said outer body encapsulated and enclosed in a cap housing,
wherein said cap is removably attached to the outlet of the syringe and a cross-section of the cap is larger than a syringe cross-section and the cap is shorter than the syringe,
wherein the expandable chamber comprises a moveable piston or an elastic fully collapsible bladder,
said syringe in fluid communication to displace said first component to said cap, mixing said first component with said second component, and to pull all of said first component and said second component from said cap into said syringe upon fully collapsing the bladder;
said expandable chamber is configured to accept the first component from the syringe and wherein the expandable chamber expands within the cap to accommodate at least all of the first component and second component;

wherein said mixing device is configured for moving the first component and the second component from the syringe to the cap and back several times;

wherein there is no pressure on said piston in an initial or storage position of said piston.

2. The mixing device of claim 1, wherein a spring is located between the moveable piston and an interior surface of the fixed outer body of the cap, wherein said spring is fully relaxed in said initial or storage position of the piston.

3. The mixing device of claim 1, wherein there is a porous mixing section or a porous absorption/desorption means or a porous filtration means within the cap or within a luer connector means securing the cap and the syringe together.

4. The mixing device of claim 3, wherein a third component is located in the luer connector means.

5. The mixing device of claim 1 further comprising at least two caps having fixed outer bodies, each attached to an exit of the syringe or to an intermediate valve, wherein at least one cap has the bladder.

6. The mixing device of claim 1 comprising a first cap attached to an exit of the syringe, and further comprising a second cap attached to a rear port on the first cap, wherein the first cap has the expandable chamber comprising the elastic fully collapsible bladder, and the second cap comprises the expandable chamber comprising a moveable piston or the expandable chamber comprising the elastic fully collapsible bladder.

7. The mixing device of claim 1, wherein the first component comprises gelatin and the second component comprises thrombin or water.

8. The mixing device of claim 1, wherein the first component comprises water and the second component comprises thrombin or gelatin.

9. The mixing device of claim 3, wherein said luer connector means comprises a static mixer.

10. The mixing device of claim 1, wherein said expandable chamber comprising the elastic fully collapsible bladder is a self-collapsible chamber.

11. A method of making and delivering a mixture, comprising:

(a) Attaching a cap having a fixed outer body and an expandable chamber therein containing a second component which is a fluid, a powder, or a paste to a syringe containing a first component which is a fluid; the cap having larger cross-section than a cross-section of the syringe and the cap being shorter than the syringe; the expandable chamber expands within the cap to accommodate all of the first and second components; said outer body encapsulated and enclosed in a cap housing;

(b) Expressing the first component from the syringe into the expandable chamber;

(c) Retrieving the first component and the second component from the expandable chamber back into the syringe;

(d) Optionally repeating steps (b) and (c) several times until the first component and the second component are thoroughly mixed;

(e) Retrieving the first component and the second component from the expandable chamber back into the syringe;

(f) Detaching the cap from the syringe leaving substantially all of the first component and the second component in the syringe; and (g) Expressing mixed said first component and the second component from the syringe onto a target, wherein the expandable chamber comprises a moveable piston or an elastic fully collapsible bladder, said syringe in fluid communication to displace said first component to said cap, mixing said first component with said second component, and pull all of said first component and said second component from said cap into said syringe upon fully collapsing the bladder;

said expandable chamber is configured to accept the first component from the syringe and wherein the expandable chamber can expand within the cap to accommodate at least all of the first component and second component;

wherein said mixing device is configured for moving the first component and the second component from the syringe to the cap and back several times;

wherein there is no pressure on said piston in an initial or storage position of said piston.

* * * * *